United States Patent

Bathe et al.

Patent Number: 5,732,693
Date of Patent: Mar. 31, 1998

[54] PAUSE CONTROL OF NITRIC OXIDE THERAPY

[75] Inventors: Duncan P. L. Bathe, Madison; Thomas S. Kohlmann, McFarland; Robert Q. Tham, Madison, all of Wis.

[73] Assignee: Ohmeda Inc., Liberty Corner, N.J.

[21] Appl. No.: 766,833

[22] Filed: Dec. 13, 1996

Related U.S. Application Data

[60] Provisional application No. 60/027,144, Oct. 2, 1996.

[51] Int. Cl.[6] .................................................. A61M 15/00
[52] U.S. Cl. ........................ 128/203.12; 128/203.14; 128/203.25
[58] Field of Search ....................... 128/203.12, 203.14, 128/203.23, 203.25, 202.22, 202.27, 204.21, 204.22, 204.23, 204.18, 205.11, 205.12, 205.23, 205.24

[56] References Cited

U.S. PATENT DOCUMENTS 5,588,083 12/1996 Bathe et al. .

Primary Examiner—Vincent Millin
Assistant Examiner—Robert N. Wieland
Attorney, Agent, or Firm—Roger M. Rathbun; Salvatore P. Pace

[57] ABSTRACT

A system for the delivery of nitric oxide therapy to a patient that allows interventions by a user by activating a pause mode through a user input. A CPU in the system recognizes the activation of the pause mode and sends a signal to close a valve in order to discontinue the supply of nitric oxide to the patient. The activation of the pause mode also deactivates the normal alarm systems. A timer is activated when the system enters the pause mode and the timer allows a predetermined amount of time to pass while the pause mode is in effect. After that predetermined period of time has elapsed, the timer causes the CPU to reopen the valve to reestablish the flow of nitric oxide for the continued therapy and reestablish the alarm systems. The pause mode can be thus carried out without changing any alarm settings, established flows and the like so that the therapy is again recommenced at the same conditions as were in effect prior to the initiation of the pause mode.

5 Claims, 2 Drawing Sheets

[1]

PAUSE CONTROL OF NITRIC OXIDE THERAPY

This application is based upon Provisional patent application Ser. No. 60/027,144 filed Oct. 2, 1996.

BACKGROUND OF THE INVENTION

This invention relates to a system for the administration of nitric oxide to a patient for therapy and, more particularly, to a system that allows the user to pause the therapy, and consequently resume the therapy, without altering the conditions of that therapy being administered to the patient prior to the pause of therapy.

Nitric oxide is generally administered to patients for various therapeutic reasons, among them, the treating or preventing of bronchoconstriction or reversible pulmonary vasoconstriction. One of such treatments is the administration of NO by means of inhalation and the treatment is more fully set forth in U.S. Pat. No. 5,485,827 of The General Hospital Corporation.

The administration of NO is accomplished by various apparatus, among them is the system disclosed in U.S. Pat. No. 5,558,083 of Ohmeda Inc. In that system, an NO containing gas is provided as a gas in mixture of another gas, such as nitrogen, and the NO containing gas is mixed in a predetermined proportion with oxygen and administered to the patient.

One difficulty in the administration of nitric oxide, however, is due to the lengthy periods of time during which the administration takes place, it is often necessary for the attending personnel to intervene with the patient, for example, to clear the patient's airway or to otherwise have the need to stop the therapy for some other need of the patient.

Those interventions are generally carried out by nurses and in carrying out the intervention, the nurse typically has two courses of action, one is to change the therapy such as to turn it off and the second is to simply remove the face mask to carry out that intervention. In the case of the former, the change of the therapy runs the risk that the nurse may leave the patient after the intervention has been completed without returning the NO therapy back to the original conditions. Thus there is the risk that the improper therapy, or no therapy at all, may be delivered to the patient. Since the NO administration apparatus has been deliberately changed, the apparatus believes the new therapy is desired and no alarms are triggered.

If, on the other hand, the nurse merely removes the face mask or other administration device to the patient without stopping the flow or affecting the therapy, the nitric oxide is released to the atmosphere and can affect the attending personnel, that is, pose a pollution problem, but also the alarms are immediately triggered and which are a nuisance.

SUMMARY OF THE INVENTION

In accordance with the present invention, there is provided a system that allows the user to pause the nitric oxide administration apparatus so that the nurse can make whatever interventions are needed to the patient without changing any of the conditions set in the apparatus. By this system, the settings of the NO administration apparatus are thus unaffected and when the pause is ended, the same conditions that existed prior to the pause are again commenced by the administration apparatus.

Accordingly, since the settings of the apparatus and thus the therapy parameters are not changes, a nurse can activate the pause and carry out the intervention. Thus, there are no changes to the alarm system established by a physician or to the flows and concentrations of gases being administered to the patient. The activation of the pause mode does, however, suppress the normal alarms so that the annoyance of alarms is eliminated during that mode.

As a safety feature, a timer is also activated when the pause is initiated and which will recommence the normal nitric oxide administration apparatus when the predetermined pause time has elapsed so that the pause time is predetermined and the therapy self initiated when the timer has determined that the pause time has elapsed.

DETAILED DESCRIPTION OF THE INVENTION

Figure 1:
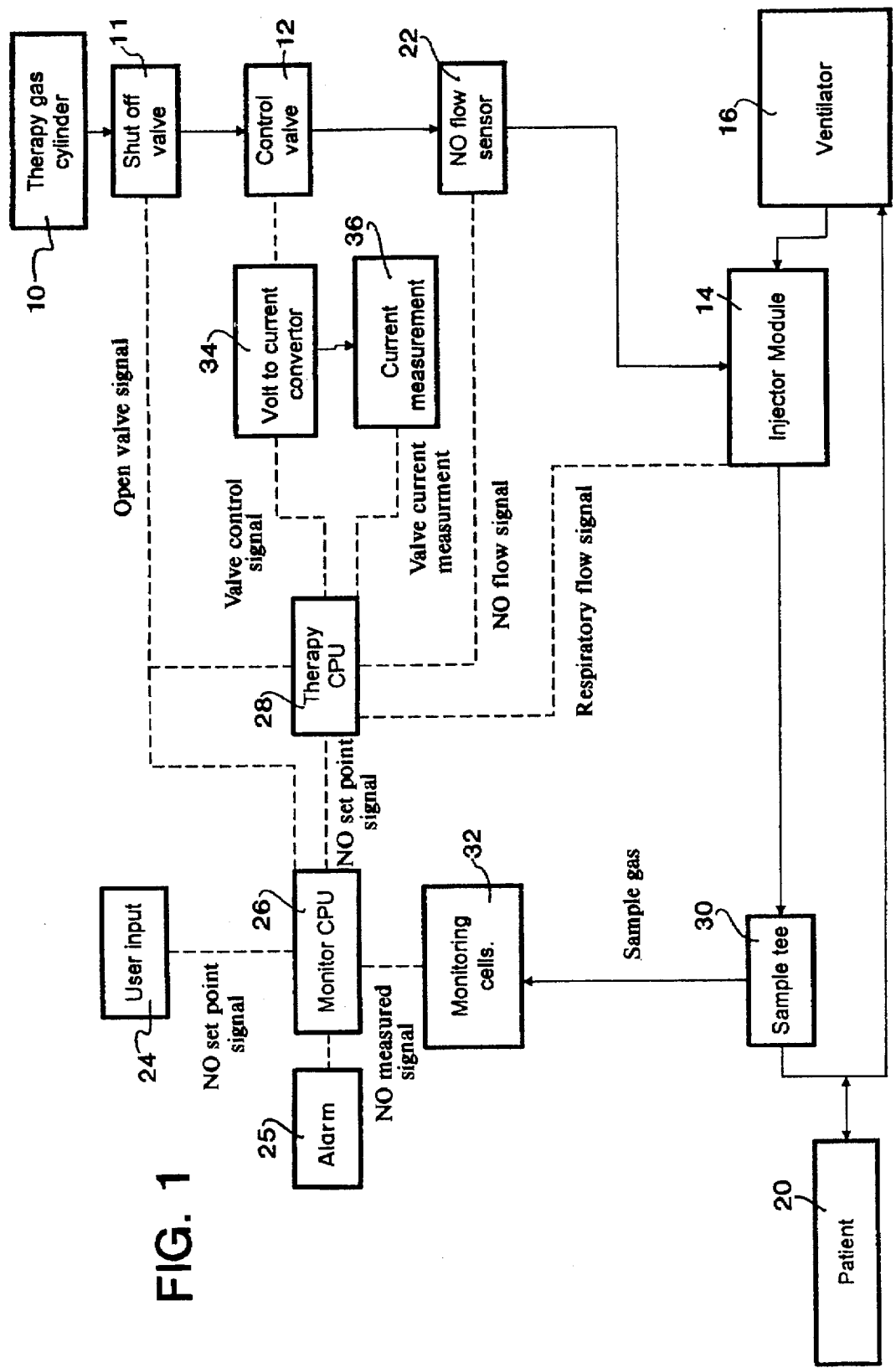
FIG. 1 is a block diagram of a nitric oxide administration system usable with the present invention in its normal operation.

Turning first to FIG. 1, there is shown a block diagram of the nitric oxide administration system used with the present invention and which is more fully described in U.S. Pat. No. 5,558,083. As shown in FIG. 1, however and which is somewhat simplified with respect to the aforementioned U.S. Patent, a supply of nitric oxide is provided in the form of a cylinder 10 of gas. That gas is preferably nitric oxide mixed with nitrogen and is commercially available in a pressurized cylinder or, may be available from a hospital piping system to supply various locations through out the patient care facility such as operating rooms. The supply of NO may, of course, be mixed with nitrogen or other gases to bring the concentration of NO down to a relatively low level.

A shut-off valve 11 is located just downstream of the gas cylinder 10 and is operable by an electrical signal to turn on or off the flow from the gas cylinder 10 as will be later explained.

A proportion gas control valve 12 is positioned with suitable conduit to receive the NO/nitrogen gas from cylinder 10 and a typical suitable proportional control valve 12 is available from Parker Hannifin Corp., Pneutronics Division, Holis, N.H. and which provides electronic control of gases. The flow of NO/nitrogen is thereafter supplied to an injector module 14 where it is mixed with air or other breathable mixture that is supplied from a gas administration device such as ventilator 16. As again will be seen, although a ventilator is shown, the supply of air or other breathable mixture to the patient may be supplied by a manually squeezed bag or other device to breath the patient The injector module mixes the breathable air from ventilator 16 with the supply of NO/nitrogen from the cylinder 10 in the amount desired by the user for ultimate supply to the patient 20. A flow sensor 22 is normally also present in the NO/nitrogen stream to the injector module 14 to monitor the NO flow.

As more detailed in the aforementioned U.S. Patent, the user selects the desired concentration of NO that is suitable for the patient therapy and inputs that selected concentration by an user input 24 into a monitor CPU 26 as a user set point signal. That signal is then transmitted to a therapy CPU 28 and which controls the proportional control valve 12 by sending a valve control signal to that proportional control valve 12 to set the valve to provide the amount of NO/nitrogen to arrive at the desired concentration of NO administered to the patient.

The user input 24 is also used by the user to establish various alarm conditions that trigger various alarms 25 as controlled by monitor CPU 26. Thus, the user can select among various alarm settings established in a CPU an which alert the user of conditional outside those alarm conditions.

The value of the valve control signal to proportional control valve 12 by the therapy CPU 28 is determined from an input from a flow sensor in the injector module 14 indicative of the flow to the patient and the desired user input set by the user. With those values, the therapy CPU 28 calculates the correct setting of the proportional control valve 12 and sends the appropriate valve control signal to the proportional control valve 12 to achieve the desired user value.

As a further check of the concentration of NO administered to the patient, a sample tee 30 is provided at a point near the patient and a sample of the gas delivered to the patient is extracted and delivered to various monitoring cells 32 where the monitors, generally electrochemical cells, monitor NO, $O_2$ and $NO_2$. Those monitored values are provided to the monitor CPU 26 to maintained track of the values administered to the patient and to inform the user that the value of NO is within a close range of the value set by the user.

Taking now, the valve control signal that is provided by the therapy CPU 28 to the proportional control valve 12, various electrical or even light signals may be used, however, in the preferred embodiment, a voltage is outputted by the therapy CPU 28 and which is converted to a proportional current in a voltage to current converter 34 and thus a current indicative of the desired position of proportional control valve 12 is inputted to proportional control valve 12. That current is preferably monitored by a current sensing device 36 and that monitored current again inputted to the therapy CPU 28.

Accordingly, as now can be seen, the user determines the desired therapy concentration of NO to be administered to the patient 20 and inputs that value with the user input 24. The user input 24 establishes a signal indicative of the desired NO concentration to the patient and sends that signal to the monitor CPU 26 and on to the therapy CPU 28. In the therapy CPU 28, a signal is determined that is to be sent to the proportional control valve 12 based on the user input signal and the flow that is being delivered to the patient through injector module 14 so that the proportional control valve 12 can provide the precise amount of NO in nitrogen to arrive at the desired user value to the patient. The signal to the proportional control valve 12 may be an electrical signal in accordance with the preferred embodiment or may be a electromagnetic signal transmitted by a fiberoptic cable or may even be a mechanical transmission.

As can be seen, the monitor CPU 26 also provides a signal to shut-off valve 11 and, in the mode set forth in FIG. 1, that signal is an open valve signal and which retains the shut-off valve in the open position so that the overall system can supply the NO therapy to patient 20.

Figure 2:
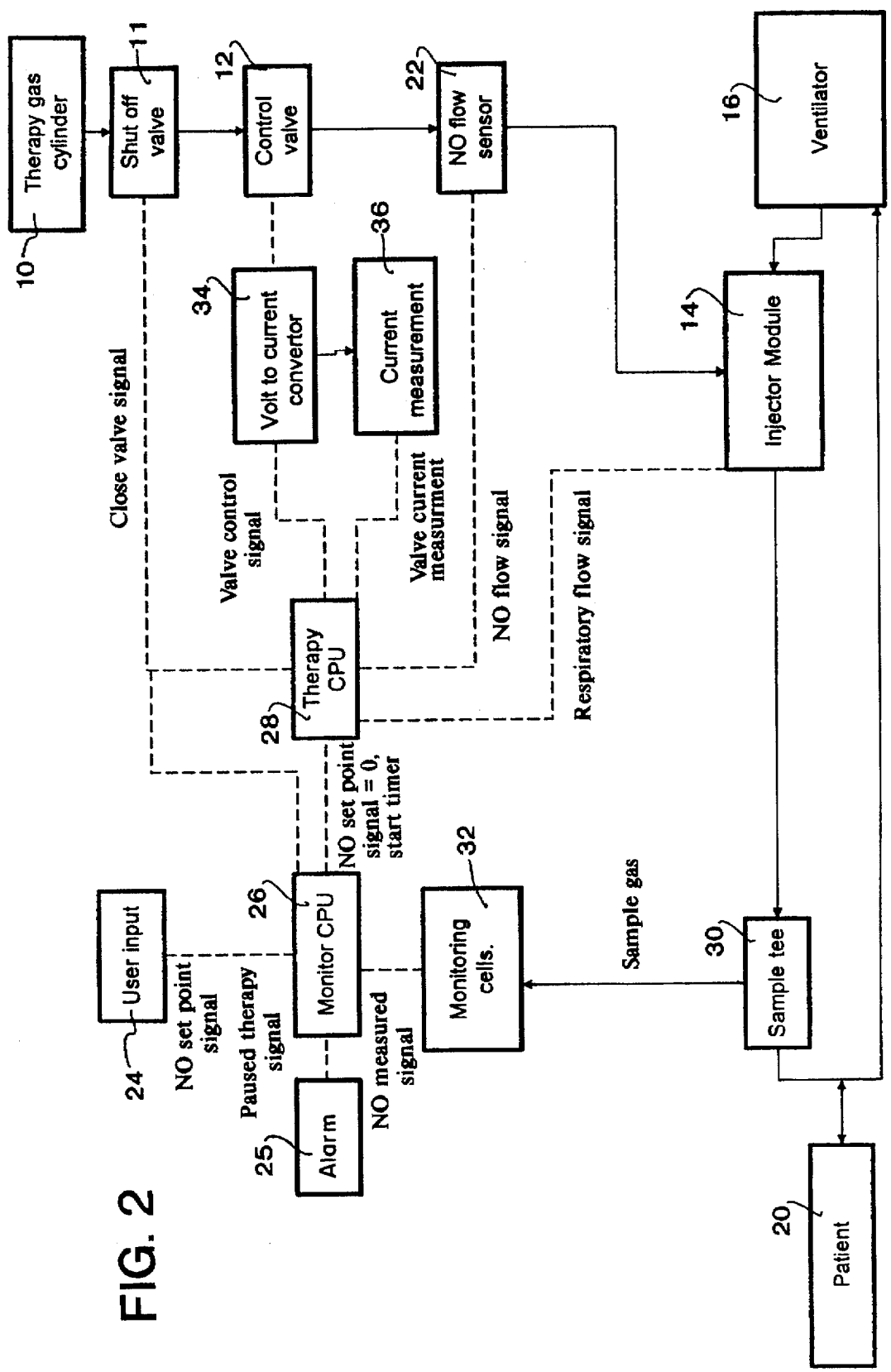
FIG. 2 is a block diagram of the system of FIG. 1 where the system is in its pause mode in carrying out the present invention.

Turning now to FIG. 2, there is shown a block diagram of the overall NO administration system when the system is in the pause mode, that is, the operator has determined the need for some intervention of the patient such as to clear the patient's airway or administer some other care to the patient. As such, the system is removed from administering NO therapy to the patient 20 so that such intervention can take place and the user puts the system into the pause mode by the user input 24. Such input may be a push-button or the like that is operated by the user.

As shown in FIG. 2, therefore, that pause therapy signal is communicated to the monitor CPU 26 to provide some indication to the user that the system is in the pause mode The monitor CPU 26 sends a signal to the shut-off valve 11 closing that valve so that the flow of NO containing gas is terminated and the therapy administration system is inactivated. That monitor CPU 26 also immediately sends a signal to the alarm 25 to prevent the sounding or visual display of any alarms when the NO administration system is in the pause mode to avoid annoyance to the user.

At this point, the overall administration system is inactivated and the user can carry out the desired intervention on the patient. It should be noted, however, that the other variables in the overall NO administration system are left unchanged, that is, the current therapy settings on the user input 24 are not changed and it is not necessary to change the flows, concentrations and the like already established by the physician.

The monitor CPU 26 also includes a timer that is activated upon receipt of the pause therapy signal and which begins the clock to time the period of the pause. That overall period can be predetermined in accordance with the manufacture or may be predetermined by the user that sets a desired pause period. As that timer reaches the predetermined time, however, a signal is automatically sent to shut-off valve 11 by the monitor CPU 26 to return the shut-off valve to the open position. Thus, the NO administration system automatically returns the delivery of therapy to the patient within a predetermined amount of time, determined by the timer, so that the user cannot inadvertently cease the therapy to the patient and leave it in the pause mode.

Upon return to the normal operating conditions, with shut-off valve 11 again opened, the system does not need readjusting or recreating the existing conditions that were in effect upon the initiation of the pause mode. Those conditions are automatically returned to the original conditions, i.e. flows, alarms and NO concentrations, in effect prior to the pause since no changes were made to those settings.

As an alternative, the monitor CPU 26 may alert the therapy CPU 28 of the user selection of the pause mode at user input 24 and the therapy CPU 28 sends its valve control signal to the control valve 12 to shut down that valve. Again, however, the timer of monitor CPU 26 is activated and a signal sent to the therapy CPU 28 at the end of the predetermined time period and the therapy CPU 28 again returns the control valve 12 to its original position to reestablish the NO therapy at the same conditions that were in effect prior to the pause mode being initiated.

Thus, the user may activate a pause mode for a predetermined time and when that pause has ended, the overall NO administration apparatus returns to its original settings and does not require the attendance of a physician to reestablish the desired therapy to the patient.

Numerous further variations and combinations of the features discussed above can be utilized without departing from the spirit of the invention as defined by the claims below. Accordingly, the foregoing description of the preferred embodiment should be taken by way of illustration rather than by way of limitation of the invention as claimed.

We claim:

1. A system for the delivery of nitric oxide for therapy to a patient by providing a flow of nitric oxide (NO) to a patient, said system having a supply of a NO containing gas, a central processing unit (CPU), and a user input for establishing the desired therapy to the patient, said system further having a pause control system comprising a shut-off valve having an open position where the flow of NO is provided to the patient at a predetermined concentration and a closed position where the flow of NO is stopped, said shut-off valve being operable between said closed and said open positions by a signal from said CPU, means on said user input operable by a user to initiate a pause in the delivery of NO to the patient, said user input providing a signal to said CPU to change said shut-off valve to the closed position, said CPU further having a timing means effective to turn said shut-off valve back to the open position after the passage of a predetermined period of time whereby the predetermined concentration of NO is reestablished to the patient, said system further having a monitoring system to determine the concentration of certain gases flowing to the patient, and an alarm system to cause an alarm when the monitored concentrations exceed limits established by the user, and wherein said CPU further disables said alarm system during the time said shut-off valve is in said closed position and reestablishes said same alarm limits established by the user when said shut-off valve is turned back to said open position.

2. A system for the delivery of nitric oxide for therapy to a patient as defined in claim 1 wherein said shut-off valve also provides a control of the mixture of NO introduced to the patient.

3. A system for the delivery of nitric oxide for therapy to a patient as defined in claim 1 wherein the predetermined amount of time is set by the user.

4. A method of delivering nitric oxide for therapy to a patient, said method comprising:

(a) providing a supply of a NO containing gas, (b) providing a central processing unit (CPU), (c) providing an alarm system having predetermined alarm limits to alert the user of certain conditions, (d) providing a user input for establishing the desired therapy to the patient, (e) providing a shut-off valve having an open position where the flow of NO is provided to the patient at a desired concentration and a closed position where the flow of NO is stopped, (f) controlling the position of said shut-of valve between said closed and open positions by a signal from said CPU, (g) initiating a pause in the delivery of NO to the patient by manually operating the user input to provide a signal to said CPU to change said shut-off valve to the closed position, (h) disabling the alarm system when said pause is initiated in step (g), and (i) timing the initiation of the pause in step (g) and returning the shut-off valve to the open position to reestablish the NO therapy at said desired concentration and reactivating the alarm system with the same predetermined alarm limits after the passage of a predetermined period of time.

5. A method of delivering nitric oxide for therapy to a patient as defined in claim 4 further including the step of:

(j) manually operating the user input to provide a signal to said CPU to change said shut-off valve to the open position to terminate the pause to reestablish the NO therapy at said desired concentration and reactivating the alarm system with the same predetermined alarm limits prior to the end of the predetermined time of step (i).

* * * * *